US006287786B1

(12) United States Patent
Kaser et al.

(10) Patent No.: US 6,287,786 B1
(45) Date of Patent: Sep. 11, 2001

(54) PHOSPHOLIPID TRANSFER PROTEIN

(75) Inventors: Matthew R. Kaser, Castro Valley; Jennifer L. Hillman, Mountain View; Mariah R. Baughn, San Leandro, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/629,774

(22) Filed: Jul. 31, 2000

Related U.S. Application Data

(63) Continuation-in-part of application No. 09/328,869, filed on Jun. 8, 1999, now Pat. No. 6,168,933.

(51) Int. Cl.[7] .................. G01N 33/53; G01N 33/566; C12P 21/06; C07K 1/00; C07K 16/00
(52) U.S. Cl. .................. 435/7.1; 435/69.1; 436/501; 530/350; 530/387.1; 530/388.1; 530/389.1
(58) Field of Search .................. 435/7.1, 7.2, 7.5, 435/69.1; 436/501; 530/300, 350, 333, 387.1, 387.9, 388.1, 389.1

(56) References Cited

PUBLICATIONS

Lin, comparative gene cloning: identification of novel human genes with Caenorhabditis elegans proteome as template. Submitted (May 17, 1999, accession No. AF 151810) to the EMBL/GenBank/DDBJ data base.*

Geijtenbeek, T.B.H. et al., "cDNA cloning and tissue–specific expression of the phosphatidylcholine transfer protein gene", *Biochem Journal*, 316: 49–55 (1996).

Chen, S. et al., "Phosphatidylcholine Transfer Protein from Porcine Liver", *Biochemistry International*, 23(2) : 377–382 (1991).

Feng, L. and D.E. Cohen, "Baculovirus–mediated expression of recombinant rat phosphatidylcholine transfer protein", *Journal of Lipid Research*, 39:1862–1869 (1998).

LaMorte, W.W. et al, "Determinants of the Selection of Phosphatidylcholine Molecular Species for Secretion into Bile in the Rat", *Hepatology*, 28(3) : 631–637 (1998).

Geijtenbeek, T.B.H. et al., "Phosphatidylcholine transfer protein from bovine liver contains highly unsaturated phosphatidylcholine species", *FEBS Letters*, 391:333–335 (1996).

Nicholas, T.E., "Pulmonary Surfactant: no mere paint on the alveolar wall", *Respirology*, 1: 247–257 (1996).

Griese, M. et al., "Pulmonary surfactant in cystic fibrosis", *European Respiratory Journal*, 10: 1983–1988 (1997).

Venkataramani, A. et al., "Abnormal Duodenal Bile Composition in Patients With Acalculous Chronic Cholecystitis", *The American Journal of Gastroenterology*, 93(3) : 434–441 (1998).

Igal, R.A. and R.A. Coleman, "Neutral lipid storage disease: a genetic disorder with abnormalities in the regulation of phospholipid metabolism", *Journal of Lipid Research*, 39: 31–43 (1998).

Alb, J.G. et al., "Phospholipid metabolism and membrane dynamics", *Current Opinion in Cell Biology*, 8: 534–541 (1996).

Cockcroft, S., "Phosphatidylinositol transfer proteins: a requirement in signal transduction and vesicle traffic", *BioEssays*, 20: 423–432 (1998).

Bolton, A.E. and W.M. Hunter, "The Labelling of Proteins to High Specific Radioactivities by Conjugation to a $^{125}$I–Containing Acylating Agent", *Biochem. Journal*, 133: 529–539 (1973).

Strausberg, R. (contact) ; "National Cancer Institute, Cancer Genome Anatomy Project (CGAP) ," Database EMBL Online! EBI; Accession No. AI219986, Oct. 28, 1998 (Oct. 28, 1998); XP002147772, abstract.

Lai, C.H. et al.; "Identification of novel human genes evolutionarily conserved in Caenorhabditis elegans by comparative proteomics"; Database EMBL Online! EBI; Accession No. AF151810, Jun. 1, 1999 (Jun. 01, 1999) ; XP002147773, abstract.

* cited by examiner

Primary Examiner—Ethan Whisenant
Assistant Examiner—Frank Lu
(74) Attorney, Agent, or Firm—Incyte Genomics, Inc.; Lynn E. Murry

(57) ABSTRACT

The invention provides a mammalian nucleic acid molecule and fragments thereof. It also provides for the use of the nucleic acid molecule for the characterization, diagnosis, or treatment of conditions, diseases and disorders associated with gene expression and for the production of a model system. The invention additionally provides expression vectors and host cells for the production of the protein encoded by the mammalian nucleic acid molecule.

7 Claims, 7 Drawing Sheets

```
              11           20           29           38           47           56
5' ATCGT TCT GTG GTC CTT TCT TTT ATG ATT CAC AAG GAA TGA CCC TCT TCA TCG CCT 65           74           83           92          101          110
   CTC CTA ATT CAG TCC TCA CAA CAG TCC TTT TAC AAA TGG GAC AAC AGG TTA GAG 119          128          137          146          155          164
   GAA GTC AGG CAG ATT TCC AGC ATC ATA GAG AGT AAA GGA CCA GGG AAG GAT CAG 173          182          191          200          209          218
   GAT TCA AGG ACT GCA CCC AGG CTC TGC TTC CAG CTT GCT GTG TGA CTT TGG GTA 227          236          245          254          263          272
   ATT TTG TTC CCT TAG GGA ACT GAG CTT TCT CAT TTG TAA ATG CAA ACA GGC TGT 281          290          299          308          317          326
   TGG GAG GAT CAA ATG AGA TCC AGG GAA AAC AGC TTA GTT TAC TTT CAG GAA 335          344          353          362          371          380
   TTT ACC CAC GCG GTA TAT AAA GGC AAA ATA TTA TTA TAG TCA GGT GAT TGT AGA
```

FIGURE 1A

```
            389        398        407        416        425        434
        TTG AGG AAC CCA TTT CCT CAT CCT GCA AAT TGC AAA CCT GAG GGC CCA AAG AGG 443        452        461        470        479        488
        GAC AGG GGC TTG CCC CAG GTC TCA GCA GGC TGT GAG CAA GAG CTA AAG CCT AAT 497        506        515        524        533        542
        CCT CCT GCC TTT GGG CCT GGA GCC CTT CCT TGT CCA GGG GTC AGT GTC TTT 551        560        569        578        587        596
        GTT GGA TAC AGG CTT AGA TTG ACT GAC TGT ACC CTG AGA ACC TAG GGG AGT CCC 605        614        623        632        641        650
        TGT TCC CAA TTC TCC TAC CCC CAC CTT GGC CTG ATG GAG GAA GAC CCT GCT 659        668        677        686        695        704
        GTG TTG AGA TGA GCA CCA GAG CCA AGA AGC TGA GGA GGA TCT GGA GAA TTC TGG 713        722        731        740        749        758
        AGG AAG AGA GTG TTG CTG GAG CTG TAC AGA CCC TGC TTC TCA GGT CCC AGG
```

FIGURE 1B

```
                                                                      812
                             794                                      AGG
                             TCG                  866                 R
              776            ACG                  ATG       920
767           GCA            GAG       848        CCC       CGT       974
TCA           GCC            CCG       CTC        CTG       GGC       TGT
GCG           TCT            CGG       ACA        CCG       CTG       TCA       1028
GTG    785    GCA    803     CTG    857 GGC    911 CCT    965 TTC    1019 TCT    1082 TGG
AAG    GCG    TCT    CCT     TCG    CTC ACA    CCC CGG    CGG AGC    GTC GGG    GAG GAG    C
        S              P       S      T   T      P   R      R   S      V   G      R   E
                                                                                           R
       821                                                                                 M
767    AGG    839            893                  947                 1001                 E
AAG    CGG    GAG            GAG                  GAC                 ACC                  1136
ACC    ACT    AGG            CCC                  GAC                 CTG                  TAC
CAG    830                   884    CAA           938  TTT            992   TAT            1046 Y
GAG    AGC           875     TCT    GGG           CCC  CGC            TGG   AGC            ATG
AGC    CGG           GCC     ACA    Q             GAT  S              AAC   Y              GAT
V             884    GCT           902                                                     D      1100
S      T             A                    938    956  F              1010  S              1064 1118
              884    A                    CCC    CGC               AGG           CAC          ACA
                                          GAT    F      956        GCT           CTG          CTC       CCC     1136
                     884    TCT           GTG    947    TTC        GGG           ACG          TAC       GAT     TAC
                     ACA    S             CAG           AGC        A             T            D         ATT     Y
                            875     CTG           AAC        AGC        TAT        AAG         GTC       GAG
                                    GCG   929                TTC        AGC        ATC         CTA       ATT
                                    A     CAG                F          Y          K           L         I
```

Bad reading — re‑outputting figure note:

FIGURE 1C

```
                    1145                   1154                   1163                   1172                   1181                   1190
            CGC AAG AAA TGG GAC AGC AAC GTC ATT GAG ACT TTT GAC ATC GCC CGC TTG ACA
             R   K   K   W   D   S   N   V   I   E   T   F   D   I   A   R   L   T 1199                   1208                   1217                   1226                   1235                   1244
            GTC AAC GCT GAC GTG GGC TAT TAC TCC TGG AGG TGT CCC AAG CCC CTG AAG AAC
             V   N   A   D   V   G   Y   Y   S   W   R   C   P   K   P   L   K   N 1253                   1262                   1271                   1280                   1289                   1298
            CGT GAT GTC ATC ACC CTC CGC TCC TGG CTC CCC ATG GGC GCT GAT TAC ATC ATT
             R   D   V   I   T   L   R   S   W   L   P   M   G   A   D   Y   I   I 1307                   1316                   1325                   1334                   1343                   1352
            ATG AAC TAC TCA GTC AAA CAT CCC AAA TAC CCA CCT CGG AAA GAC TTG GTC CGA
             M   N   Y   S   V   K   H   P   K   Y   P   P   R   K   D   L   V   R 1361                   1370                   1379                   1388                   1397                   1406
            GCT GTG TCC ATC CAG ACG GGC TAC CTC ATC CAG GTG CCC AAA ACA GGG CCC AAG AGC TGC
             A   V   S   I   Q   T   G   Y   L   I   Q   V   P   K   T   G   P   K   S   C 1415                   1424                   1433                   1442                   1451                   1460
            GTC ATC ACC TAC CTG GCC CAG GTG GAC CCC AAA GGC AGC TCC TTA CCC AAG TGG GTG
             V   I   T   Y   L   A   Q   V   D   P   K   G   S   L   P   K   W   V 1469                   1478                   1487                   1496                   1505                   1514
            GTG AAT TCT CAG TTC CTG GCT CCC AAG ATG AAG GCC AAG AAG ATG TAC AAG
             V   N   S   Q   F   L   A   P   K   M   K   A   K   K   M   Y   K
```

FIGURE 1D

```
       1523              1532              1541              1550              1559              1568
GCG TGC CTC AAG TAC CCC GAG TGG AAA CAG AAG CAC CTG CCT CAC TTC AAG CCG
 A   C   L   K   Y   P   E   W   K   Q   K   H   L   P   H   F   K   P 1577              1586              1595              1604              1613              1622
TGG CTG CAC CCG GAG CAG AGC CCG TTG AGC CTG GCG CTG TCG GAG CTG TCG
 W   L   H   P   E   Q   S   P   L   S   L   A   L   S   E   L   S 1631              1640              1649              1658              1667              1676
GTG CAG CAT GCG GAC TCA CTG GAG AAC ATC GAG AGC AGC GCG GTG GCC GAG AGC
 V   Q   H   A   D   S   L   E   N   I   D   E   S   S   A   V   A   E   S 1685              1694              1703              1712              1721              1730
AGA GAG CGG ATG GGC GGC GCG GGC GAG AGC GAC GAC AGC GAC GAC ACC TCG
 R   E   R   M   G   G   A   G   E   S   D   D   S   D   D   T   S 1739              1748              1757              1766              1775              1784
CTC ACC TGA GCC CAC CGC TTC CGC AGG GAC GGA GAC AGG ACC CGG GCC CTG
 L   T 1793              1802              1811              1820              1829              1838
GGG CGG CCG CTC CTG CAC CTG CAC TTT CTC CCC TCC CCC ACC CGG CAC CTG GTG GCA 1847              1856              1865
CCG GGC CAG GCC CAG GCG GGT GCT GCA  3'
```

FIGURE 1E

```
1772859   66 HKIKCRMECCDVPAETLYDVLHDIEYRKKWDSNVIETFDIARLTVNADVGYYSWRCPKPL 125
             +K+  +E C  PA  L DV  D++YRK+WD     V E ++   +    V Y+ + P PL
GI 897786 14 YKVFGVLEGCS-PA-LLADVYMDLDYRKQWDQYVKELYE--KESDEQMVAYWEVKYPFPL  69

1772859  126 KNRDVITLRSWLPMGAD----YIIMNYSVKHPKYPPRKDLVRAVSIQTGYLIQSTGPK-S 180
             NRD + R   +     D    Y+++  S+ P++P +   ++R    +    I+S G K S
GI 897786 70 SNRDYVYTRQRRDLDVDRRKIYVVLAQSISAPQFPEKSGVIRVKQYKQSLAIESDGKKGS 129

1772859  181 CVITYLAQVDPKGSLPKWVNKSSQFLAPKAMKMYKACLKY 222
             V  Y  +P G +P W++N +++  P  +K M KAC  Y
GI 897786 130 RVFMYYFD-NPGGQIPSWLINWAAKNGVPNFLKDMVKACQNY 170
```

FIGURE 2

FIGURE 3

| Library | Clones | Description | Abs Abund | % Abund |
|---|---|---|---|---|
| KIDNTUP03 | 12069 | kidney tumor, clear cell type cancer, pool, NORM, 3' CGAP | 10 | 0.0829 |
| LARYTUP01 | 1392 | larynx tumor, squamous cell CA, 3' CGAP | 1 | 0.0718 |
| LUNGTUP06 | 6216 | lung tumor, squamous cell CA, pooled, NORM, CGAP | 2 | 0.0322 |
| LUNGTUP04 | 17680 | lung tumor, neuroendocrine carcinoid, pool, NORM, 3' CGAP | 5 | 0.0283 |
| LUNGNON03 | 12215 | lung, mw/mets osteoSAR, aw/pleura mets, 58M, NORM | 1 | 0.0082 |
| NPOLNOT01 | 3496 | nose, nasal polyp, eosinophilia, aw/asthma, 78M | 1 | 0.0286 |
| EOSIHET02 | 9312 | periph blood, eosinophils, hypereosinophilia, 48M | 1 | 0.0107 |
| COLNTUP19 | 789 | colon tumor, adenoCA, 3' CGAP | 1 | 0.1267 |
| COLHTUS02 | 2499 | colon tumor, adenoCA, hepatic flexure, 55M, SUB, m/COLATMT01 | 1 | 0.0400 |
| COLNTUP16 | 8513 | colon tumor, adenoCA, pool, NORM, 3'/5' CGAP | 3 | 0.0352 |
| COLNTUP08 | 3175 | colon tumor, adenoCA, 3' CGAP | 1 | 0.0315 |
| COLNTUP09 | 3513 | colon tumor, adenoCA, NORM, 3' CGAP | 1 | 0.0285 |
| COLNTUP15 | 12085 | colon tumor, adenoCA, pool, NORM, 3' CGAP | 3 | 0.0248 |
| COLNTUP07 | 4187 | colon tumor, adenoCA, NORM, SUB, CGAP | 1 | 0.0239 |
| COLNNON03 | 3356 | colon, mw/adenoCA, aw/node mets, 60M, NORM, m/COLNTUT16 | 1 | 0.0298 |
| COLNNOT16 | 4807 | colon, mw/adenoCA, sigmoid, aw/node mets, 62M, m/COLNTUT03 | 2 | 0.0416 |
| PROSTUT20 | 3745 | prostate tumor, adenoCA, 58M | 2 | 0.0534 |
| PROSTUS08 | 3993 | prostate tumor, adenoCA, 59M, SUB, m/PROSNOT19 | 2 | 0.0501 |
| PROSTUS20 | 4550 | prostate tumor, adenoCA, 59M, SUB, m/PROSNOT19 | 2 | 0.0440 |
| PROSTUT01 | 3226 | prostate tumor, adenoCA, 50M, m/PROSNOT02 | 1 | 0.0310 |
| PROSTUT08 | 3757 | prostate tumor, adenoCA, 60M, m/PROSNOT14 | 1 | 0.0266 |
| PROSTUS19 | 4087 | prostate tumor, adenoCA, 59M, SUB, m/PROSNOT19 | 1 | 0.0245 |
| PROSNOT06 | 8828 | prostate, AH, mw/adenoCA, 57M, m/PROSTUT04 | 1 | 0.0113 |
| PROSBPT06 | 3367 | prostate, AH, mw/adenoCA, 66M | 2 | 0.0594 |
| PROSDIN01 | 3427 | prostate, AH, mw/adenoCA, 66M, NORM, m/PROSTUT10 | 2 | 0.0584 |
| PROSNOT16 | 7368 | prostate, AH, mw/adenoCA, 68M | 1 | 0.0136 |

PHOSPHOLIPID TRANSFER PROTEIN

This application is a continuation-in-part of U.S. Ser. No. 09/328,869 filed Jun. 8, 1999, now U.S. Pat. No. 6,168,933.

FIELD OF THE INVENTION

This invention relates to nucleic acid molecules encoding a new mammalian protein and to the use of these molecules in the characterization, diagnosis, and treatment of conditions such as disorders associated with cell proliferation, lipid metabolism and transport.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general activity. Comparisons of human gene sequences with those from other organisms where structure and/or function are known allow researchers to draw analogies and to develop model systems for testing hypotheses. These model systems are of great importance in developing and testing diagnostic and therapeutic agents for human conditions, diseases, and disorders.

The phospholipid transfer protein family, important in phospholipid trafficking, includes phosphatidylinositol transfer protein (PI-TP, identical to yeast SEC 14p), non-specific lipid transfer protein (nsL-TP, identical to sterol carrier protein 2), and phosphatidylcholine transfer protein (PC-TP). The sequence of PC-TP is unique and unrelated to other cytosolic lipid transfer proteins. It is encoded by a single gene and appears to be present in all eukaryotes (Geijtenbeek et al. (1996) Biochem J 316:49–55). Although amino acid compositions, molecular weights, and elution profiles of bovine and porcine PC-TP differ markedly, they retain similar transfer activity levels suggesting that amino acid composition of PC-TP can be altered without changing activity and specificity (Chen et al. (1991) Biochem Int 23:377–382).

PC-TP catalyzes PC intermembrane transfer (Feng and Cohen (1998) J Lipid Res 39:1862–1869), and certain PC molecular species are secreted preferentially into bile. Using multivariate analysis, LaMorte et al. (1998; Hepatology 28:631–637) examined the relationship between PC structure and the probability that individual PC species are secreted into the bile. They suggest that the likelihood of a PC being secreted into bile is closely related to its binding affinity for PC-TP.

Bovine liver PC-TP binds one molecule of PC non-covalently. Bound PC is not the predominant molecular species representative of bovine liver. Although PC species carrying a palmitoyl chain at the sn-1 position are abundant in bovine liver, they are rarely found bound as PC-TP. These findings led Geijtenbeek et al. (1996; FEBS Lett 391:333–335) to suggest that PC-TP may have a role in the metabolism of highly unsaturated, stearoyl-containing PC molecular species.

PC is implicated in many different diseases relating to phospholipid metabolism, including neutral lipid storage disease (NLSD), lung diseases such as atelectasis, edema, and cystic fibrosis, and cholecystitis (Nicholas (1996) Respirology 1:247–257; Griese et al. (1997) Eur Respir J 10:1983–1988; and Venkataramani et al. (1998) Am J Gastroenterol 93:434–441). NLSD is a genetic disorder causing abnormalities in the regulation of phospholipid metabolism. Igal and Coleman (1998; J Lipid Res 39:31–43) suggest that an underlying regulatory defect in NLSD alters the rates of synthesis and degradation of the major cellular phospholipids including phosphatidylcholine and phosphatidylethanolamine.

Phosphatidylinositol-transfer proteins are important in vesicle-trafficking and signal-transduction (Cockcroft (1998) Bioessays 20:423–432; Alb et al. (1996) Curr Opin Cell Biol 8:534–541). Because PC-TP is a member of the family containing PI-TP, catalyzes PC intermembrane transfer (Feng and Cohen, supra), and is found in many organs (lung, kidney, testis, liver, etc.); PC is implicated in vesicle trafficking disorders and transport disorders. Therefore, the ability to control PC-TP provides the ability to intercede in disease processes.

The discovery of a nucleic acid molecule encoding a phospholipid transfer protein provides new compositions which are useful in the characterization, diagnosis, and treatment of disorders associated with cell proliferation, lipid metabolism and transport.

SUMMARY OF THE INVENTION

The invention is based on the discovery of a nucleic acid molecule encoding a mammalian protein, phospholipid transfer protein (PTP), which satisfies a need in the art by providing new compositions useful in the characterization, diagnosis, and treatment of conditions such as disorders associated with cell proliferation, lipid metabolism and transport.

The invention provides an isolated and purified mammalian nucleic acid molecule comprising SEQ ID NO:1 or a fragment thereof (SEQ ID NOs:3–11). The invention further provides fragments homologous to the mammalian nucleic acid molecules from rat identified as SEQ ID NOs:12–16 in the Sequence Listing. The invention also provides a substantially purified mammalian nucleic acid molecule encoding the amino acid sequence of SEQ ID NO:2 or a portion thereof.

The invention further provides an isolated and purified nucleic acid molecule or a fragment thereof which hybridizes under high stringency conditions to the nucleic acid sequence of SEQ ID NO:1. The invention also provides an isolated and purified nucleic acid molecule or a fragment thereof which is complementary to the nucleic acid sequence of SEQ ID NO:1. In one aspect, a single stranded complementary RNA or DNA molecule is used as a probe and hybridizes under high stringency conditions to the mammalian nucleic acid sequence or a fragment thereof.

The invention further provides a method for detecting a nucleic acid molecule in a sample, the method comprising the steps of hybridizing the probe to at least one nucleic acid sequence of the sample, thereby forming a hybridization complex; and detecting the hybridization complex, wherein the presence of the hybridization complex correlates with the presence of a nucleic acid sequence in the sample. In one aspect, the method further comprises amplifying the nucleic acid sequence prior to hybridization. The nucleic acid molecule or fragment thereof may comprise either an element or a target on a microarray. The invention also provides a method for using a nucleic acid sequence or a fragment thereof to screen a library of molecules to identify at least one molecule which specifically binds the nucleic acid sequence, the method comprising providing a library of molecules, combining the nucleic acid sequence with the library of molecules under conditions allowing specific binding, and detecting specific binding, thereby identifying a molecule which specifically binds the nucleic acid sequence. Such libraries include DNA and RNA molecules, peptides, PNAs, proteins, and the like which are potential regulators of replication, transcription, and translation. In an analogous method, the nucleic acid molecule or a fragment thereof is used to purify a ligand.

The invention also provides an expression vector containing at least a fragment of the nucleic acid molecule of SEQ ID NO:1. In another aspect, the expression vector is contained within a host cell. The invention further provides a method for producing a protein, the method comprising the steps of culturing the host cell under conditions for the expression of the protein and recovering the protein from the host cell culture. The invention also provides an isolated and purified protein comprising the amino acid sequence of SEQ ID NO:2 or a portion thereof. Additionally, the invention provides a pharmaceutical composition comprising a substantially purified protein having the amino acid sequence of SEQ ID NO:2 or a portion thereof in conjunction with a pharmaceutical carrier.

The invention further provides a method for using a portion of the protein to produce antibodies. The invention also provides a method for using a protein or a portion thereof to screen a library of molecules to identify at least one molecule which specifically binds the protein, the method comprising providing a library of molecules, combining the protein with the library of molecules under conditions allowing specific binding, and detecting specific binding, thereby identifying a molecule which specifically binds the protein. In one aspect, a molecule identified using the method modulates the activity of the protein. In an analogous method, the protein or a portion thereof is used to purify a ligand.

The invention further provides a method for inserting a marker gene into the genomic DNA of a mammal to disrupt the expression of the natural mammalian nucleic acid molecule. The invention also provides a method for using SEQ ID NO:1 to produce a mammalian model system, the method comprises constructing a vector containing SEQ ID NO:1; introducing the vector into a totipotent mammalian embryonic stem cell; selecting an embryonic stem cell with the vector integrated into genomic DNA; microinjecting the selected cell into a mammalian blastocyst, thereby forming a chimeric blastocyst; transferring the chimeric blastocyst into a psuedopregnant dam, wherein the dam gives birth to a chimeric mammal containing at least one additional copy of SEQ ID NO:1 in its germ line; and breeding the chimeric mammal to generate a homozygous mammalian model system.

BRIEF DESCRIPTION OF THE FIGURES AND TABLE

FIGS. 1A, 1B, 1C, 1D, and 1E show the nucleic acid molecule (SEQ ID NO:1) encoding the amino acid sequence (SEQ ID NO:2) of the mammalian protein. The alignment was produced using MACDNASIS PRO software (Hitachi Software Engineering, South San Francisco Calif.).

FIG. 2 shows the alignment between SEQ ID NO:1 and SEQ ID NO:17 (mouse lung PC-TP; GI 897786) produced using the MEGALIGN program (DNASTAR, Madison Wis.).

FIG. 3 shows the northern analysis of tissues in which the nucleic acid molecule has altered or specific expression, particularly colon, lung, kidney and prostate. Column 1 is the library; column 2, the number of clones sequenced; column 3, the description of the tissue; column 4, the absolute abundance of transcripts; and column 5, the percent abundance.

Table 1 shows the Incyte clones from human and rat which have homology with SEQ ID NO:1 and includes their nucleotide length, biological source, region of overlap with SEQ ID NO:1, and percent identity with SEQ ID NO:1.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"PTP" refers to a purified protein obtained from any mammalian species, including murine, bovine, ovine, porcine, rodent, canine, simian, and preferably the human species, and from any source, whether natural, synthetic, semi-synthetic, or recombinant.

"Biologically active" refers to a protein having structural, immunological, regulatory, or chemical functions of a naturally occurring molecule.

"Complementary" refers to the natural hydrogen bonding by base pairing between purines and pyrimidines. For example, the sequence A-C-G-T forms hydrogen bonds with its complements T-G-C-A or U-G-C-A. The degree of complementarity between nucleic acid strands affects the efficiency and strength of the hybridization and amplification reactions.

"Derivative" refers to the chemical modification of a nucleic acid molecule or protein sequence. Chemical modifications of a molecule can include replacement of hydrogen by an alkyl, acyl, or amino group or glycosylation, pegylation, or any similar process which retains or enhances biological activity or lifespan of the molecule.

"Fragment" refers to an Incyte clone or any part of a nucleic acid molecule which retains a usable, functional characteristic.

"Hybridization complex" refers to a complex between two nucleic acid molecules by virtue of the formation of hydrogen bonds between purines and pyrimidines.

"Ligand" refers to any molecule or compound which will bind to a complementary site on a nucleic acid molecule or protein.

"Modulates" refers to a change in activity (biological, chemical, or immunological) or lifespan resulting from specific binding between a molecule or compound (i.e., ligand) and either a nucleic acid molecule or a protein.

The term "molecules" is used substantially interchangeably with the terms agents and compounds. Such molecules modulate the activity of nucleic acid molecules or proteins of the invention and may be composed of at least one of the following: inorganic and organic substances including nucleic acids, proteins, carbohydrates, fats, and lipids.

"Nucleic acid molecule" refers to a nucleic acid, oligonucleotide, polynucleotide or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA).

"Oligonucleotide" is substantially equivalent to the terms amplimer, primer, oligomer, element, target, and probe and is preferably a single stranded useful fragment of a nucleic acid molecule. Oligonucleotides can be used in hybridization or amplification technologies or in the regulation of replication, transcription or translation.

"Protein" refers to an oligopeptide, peptide, or polypeptide or portions thereof whether naturally occurring or synthetic.

"Portion", as used herein, refers to any part of a protein used for any purpose, but specifically for screening a library or plurality of molecules to identify a ligand or for the production of antibodies.

"Sample" is used in its broadest sense. A sample may comprise a bodily fluid; an extract from a cell; a chromosome, organelle, or membranes from cells; genomic DNA, RNA, or cDNA in solution or bound to a substrate; a cell; a tissue or tissue print; media in which cells were cultured or lysed, and the like.

Molecules which "specifically bind" the mammalian nucleic acid molecule or protein may include, nucleic acids, carbohydrates, lipids, proteins, or any other organic or inorganic molecules or their compounds which stabilize or modulate the activity of the mammalian protein.

"Purified" refers to nucleic acid molecule or amino acid sequences that are isolated from their natural environment and are from about 60% to about 90% free from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The invention is based on the discovery of a new mammalian nucleic acid molecule which encodes a mammalian protein, phospholipid transport protein (PTP), and the use of the nucleic acid molecule, or fragments thereof, and amino acid sequences, or portions thereof, as compositions in the characterization, diagnosis, and treatment of conditions such as disorders associated with cell proliferation, lipid metabolism and transport.

Nucleic acids encoding the mammalian protein of the present invention were identified by BLAST analysis using Incyte clone number 700137522 (SEQ ID NO:15) from the rat liver library (RALINOT01) which was differentially expressed in male rat reproductive tissue. A consensus sequence, SEQ ID NO:1, was assembled from the following overlapping and/or extended nucleic acid fragments found in Incyte Clones 3591822F6, 745516R6, 1807728F6, 1772859H1, 1505466H1, 798614H1, 4114738H1, 1923871H1, and 2013709H1; SEQ ID NOs:3–11, respectively. FIGS. 1A, 1B, 1C, 1D, and 1E show the consensus sequence and translation of SEQ ID NO:1. FIG. 3 shows northern analysis of this sequence in various libraries, particularly reproductive, gastrointestinal, and respiratory tissues. SEQ ID NO:1 has a 70% association with cancerous or proliferating tissues and a 22% association with inflamed, immune responsive, or infected tissues. Of particular note is expression in tissues from subjects with eosinophilia, adenocarcinomas of the colon and prostate, squamous cell carcinomas of the respiratory system, and clear cell type cancer of the kidney. SEQ ID NO:2 or an antibody to the protein are particularly useful to diagnose adenocarcinoma of the colon.

In one embodiment, the protein comprising the amino acid sequence of SEQ ID NO:2, PTP, is 291 amino acids in length and has three potential N-glycosylation sites at residues N44, N147, and N201; four potential casein kinase II phosphorylation sites at residues S35, T81, S271, and S284; and four potential protein kinase C phosphorylation sites at residues S32, S118, T132, and S149. The oligopeptides from residue H66 to residue A79 or from residue L82 to residue S97 of SEQ ID NO:2, are useful for purifying a ligand or for antibody production. The protein has chemical and structural similarity with mouse lung PC-TP (GI 897786; SEQ ID NO:17). In particular, as shown in FIG. 2, PTP and the mouse lung PC-TP protein share 31% identity and 52% similarity from residue H66 through residue Y222 of PTP (FIG. 2).

Table 1 shows the nucleic acid fragments from human and rat and their sequence coverage and identity with SEQ ID NO:1. Columns 1 and 2 list the SEQ ID NO and Incyte clone number, respectively, for each nucleic acid fragment. The fragments of SEQ ID NO:1, SEQ ID NOs:3–11, are useful in hybridization or amplification technologies to identify and distinguish between the mammalian protein disclosed herein and similar sequences including SEQ ID NOs:12–16. Column 3 lists the nucleotide length for each fragment. Columns 4 and 5 identify the source organism and Incyte cDNA library from which the fragments were isolated, respectively. Column 6 identifies the range of nucleotide residues in SEQ ID NO:1 over which each fragment shows identity. Column 7 shows the percent sequence identity between each fragment and SEQ ID NO:1 over the nucleotides set forth in column 6.

The mammalian fragments comprising SEQ ID NO:12–16 from rat, were identified using either SEQ ID NO:1 or one of the Incyte clones, SEQ ID NOs:3–11. Any of these sequences may be used in hybridization and amplification technologies to identify and distinguish between SEQ ID NO:1 and similar sequences in a sample. The sequences may be used to produce transgenic animal models which mimic human conditions, diseases, or disorders or to monitor animal toxicology studies, clinical trials, and subject/patient treatment profiles.

Characterization and Use of the Invention cDNA libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequence was chemically and/or electronically assembled from fragments including Incyte clones, extension, and/or shotgun sequences using computer programs such the AUTOASSEMBLER application (Applied Biosystems, Foster City Calif.).

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase, thermostable T7 DNA polymerase (Amersham Pharmacia Biotech (APB), Piscataway N.J.), or combinations of polymerases and proofreading exonucleases such as those found in the ELONGASE amplification system (Life Technologies, Rockville Md.). Preferably, sequence preparation is automated with machines such as the MICROLAB 2200 system (Hamilton, Reno Nev.), and the DNA ENGINE thermal cycler (PTC200; MJ Research, Watertown Mass.). Machines used for sequencing include the ABI 3700 or 377 DNA sequencing systems (Applied Biosystems) and the MEGABACE 1000 DNA sequencing system (APB). The sequences may be analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative of regions flanking the nucleic acid molecules of interest. Prefinished sequences (incomplete assembled sequences) are inspected for identity using various algorithms or programs well known in the art, CONSED (Gordon (1998) Genome Res 8:195–202). Contaminating sequences including vector or chimeric sequences or deleted sequences can be removed or restored, respectively, organizing the prefinished sequences into finished sequences.

Extension of the Nucleic Acid Sequence

The sequences of the invention may be extended using various PCR-based methods known in the art. For example, the XL-PCR kit (Applied Biosystems), nested primers, and commercially available DNA libraries (Clontech, Palo Alto Calif.) may be used to extend the nucleotide sequence. For all PCR-based methods, primers may be designed using commercially available software, such as OLIGO 4.06 Primer Analysis software (National Biosciences, Plymouth Minn.) to be about 22 to 30 nucleotides in length, to have a GC content of about 50% or more, and to anneal to a target sequence at temperatures from about 55° C. to about 68° C. When extending a sequence to recover regulatory elements, it is preferable to use genomic, rather than cDNA libraries.

USE OF THE MAMMALIAN NUCLEIC ACID MOLECULE

Hybridization

The nucleic acid molecule of SEQ ID NO:1 and fragments thereof can be used in various hybridization technologies for various purposes. Hybridization probes may be designed or derived from SEQ ID NO:1. Such probes may be made from a highly specific region such as the 5' regulatory region or from a conserved motif, and used in protocols to identify naturally occurring molecules encoding the mammalian protein, allelic variants, or related molecules, and should preferably have at least 50% amino acid sequence identity to any of the protein sequences. The hybridization probes of the subject invention may be DNA or RNA and may be derived from the molecule of SEQ ID NO:1 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid molecule may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are completely complementary. In some membrane-based hybridizations, perferably 35% or most preferably 50%, formamide can be added to the hybridization solution to reduce the temperature at which hybridization is performed, and background signals can be reduced by the use of other detergents such as Sarkosyl or TRITON X-100(Sigma-Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., U.S. Pat. No. 5,474,796; Schena et al. (1996) Proc Natl Acad Sci 93:10614–10619; PCT application WO95/251116; PCT application WO95/35505; Heller et al. (1997) Proc Natl Acad Sci 94:2150–2155; and U.S. Pat. No. 5,605, 662.)

Hybridization probes are also useful in mapping the naturally occurring genomic sequence. The sequences may be mapped to a particular chromosome, to a specific region of a chromosome, or to artificial chromosome constructions, e.g., human artificial chromosomes, yeast artificial chromosomes, bacterial artificial chromosomes, bacterial P1 constructions, or single chromosome DNA libraries.

Expression

A multitude of nucleic acid molecules capable of encoding the mammalian protein may be cloned into a vector and used to express the protein, or portions thereof, in host cells. The nucleotide sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and 3' untranslated regions) from various sources which have been selected for their efficiency in a particular host. The vector, nucleic acid sequence, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. Sequences may be ligated into the E1 or E3 region of the viral genome, and the infective virus used to transform and express the protein in host cells. The Rous sarcoma virus enhancer or SV40 or EBV-based vectors may also be used for high-level protein expression Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian nucleic acid molecule is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas, Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative and the resin is washed. The full length peptide is synthesized by sequential deprotection, coupling of derivitized amino acids, and washing with dichloromethane and/or N, N-dimethylformamide. The peptide is cleaved between the peptide carboxyterminus and the linker group to yield a peptide acid or amide. (Novabiochem 1997/98 Catalog and Peptide Synthesis Handbook, San Diego Calif., pp. S1–S20). Automated synthesis may also be carried out on machines such as the ABI 431A Peptide synthesizer (Applied Biosystems). A protein or portion thereof may be substantially purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including goats, rabbits, rats, mice, humans, and others may be immunized by injection with mammalian protein or any portion thereof. Adjuvants such as Freund's, mineral gels, and surface active substances such as lysolecithin, pluronic polyols, polyanions, peptides, oil emulsions, keyhole limpet hemocyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J Immunol Methods 81:31–42; Cote et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian protein may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or APB kits for incorporation of a labeled nucleotide such as $^{32}$p-dCTP, Cy3-dCTP or Cy5-dCTP or amino acid such as $^{35}$S-methionine (APB). Nucleic acids and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTICS

The nucleic acid molecules, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with altered expression of PTP include eosinophilia, adenocarcinomas of the colon and prostate, squamous cell carcinomas of the respiratory system, and clear cell type cancer of the kidney (FIG. 3. The nucleic acid molecule of SEQ ID NO:2 or an antibody to the protein is particularly useful to diagnose adenocarcinoma of the colon. The diagnostic assay may use hybridization or amplification technology to compare gene expression in a biological sample from a patient to standard samples in order to detect altered gene expression. Qualitative or quantitative methods for this comparison are well known in the art.

For example, the nucleotide sequence may be labeled by standard methods and added to a biological sample from a patient under conditions for the formation of hybridization complexes. After an incubation period, the sample is washed and the amount of label, or its signal, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a sequence or a fragment thereof under conditions for hybridization or amplification. Standard hybridization may be quantified by comparing the values obtained from normal subjects with values from an experiment in which a known amount of a substantially purified nucleic acid molecule is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-Interscience, New York N.Y.; and Pound, supra.)

THERAPEUTICS

Chemical and structural similarity, e.g., in the context of sequences and motifs, exists between regions of the PTP and phospholipids from rat. In addition, PTP is expressed in tissues from subjects with eosinophilia, adenocarcinomas of the colon and prostate, squamous cell carcinomas of the respiratory system, and clear cell type cancer of the kidney. These disorders have components that are closely associated with cell proliferation, lipid metabolism and transport. In the treatment of conditions associated with increased expression or activity, it is desirable to decrease expression or protein activity. In the treatment of conditions associated with decreased expression or activity, it is desirable to increase expression or protein activity.

In one embodiment, a composition comprising a substantially purified mammalian protein in conjunction with a pharmaceutical carrier may be administered to a subject to treat a condition associated with altered lifespan, expression, or activity of the mammalian protein including, but not limited to, those provided above.

In a further embodiment, a ligand which modulates the activity of the mammalian protein may be administered to a subject to treat a condition associated with altered lifespan, expression, or activity of the protein including, but not limited to, those listed above. In one aspect, an antibody which specifically binds the mammalian protein may be used as a targeting or delivery mechanism for bringing a pharmaceutical agent to cells or tissue which express the mammalian protein.

In an additional embodiment, a vector capable of expressing or suppressing the mammalian protein thereof may be administered to a subject to treat a condition associated with altered lifespan, expression, or activity of protein including, but not limited to, those described above.

Any of the nucleic acids molecules or fragments thereof or proteins or portions thereof, vectors delivering these molecules, and their ligands may be administered in combination with other therapeutic agents. Selection of the agents for use in combination therapy may be made by one of ordinary skill in the art according to conventional pharmaceutical principles. A combination of therapeutic agents may act synergistically to effect treatment of a particular condition at a lower dosage of each agent.

Modification of Gene Expression Using Nucleic Acids

Gene expression may be modified by designing complementary sequences or antisense molecules (DNA, RNA, or PNA) to the control, 5', 3' or regulatory regions of the mammalian gene. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177.) A complementary sequence may also be designed to block translation by preventing binding between ribosomes and mRNA. In one alternative, a library of nucleic acid molecules or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening Assays

The nucleic acid molecule encoding the mammalian protein may be used to screen a library of molecules for specific binding affinity. The assay can be used to screen a library of DNA molecules, RNA molecules, PNAs, peptides, or proteins including transcription factors, enhancers, repressors, and the like which modulate or regulate the activity of the nucleic acid molecule in the biological system. The assay involves providing a library of molecules, combining the mammalian nucleic acid molecule or a fragment thereof with the library of molecules under conditions allowing specific binding, and detecting specific binding to identify at least one molecule which specifically binds the nucleic acid molecule.

Similarly, the nucleic acid molecule or a fragment thereof may be used to purify a ligand from a sample (cf. protein example below). A method for using a mammalian protein or a portion thereof to purify a ligand would involve providing a sample, combining the protein with the sample under conditions to allow specific binding, and detecting specific binding, recovering the bound protein, and using an appropriate agent to separate the protein from the purified ligand.

Likewise the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, and the like, ligands which specifically bind the protein. One method for high throughput screening using very small assay volumes and very small amounts of test compound is described in U.S. Pat. No. 5,876,946 which screens large numbers of molecules for enzyme inhibition or receptor binding.

Conversely, the protein may be used to purify a pharmaceutical agent from a very large sample volume. A method for using a mammalian protein to purify a pharmaceutical agent would involve providing a sample, for example, media containing cell products; combining the protein with the sample under conditions to allow specific binding; recovering the bound protein; and then using an appropriate chaotropic agent to separate the protein from the purified pharmaceutical agent. Exemplary pharmaceutical agents would be a chimeric antibody, a single chain antibody, a Fab fragment or a F(ab')2 fragment.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

MODEL SYSTEMS

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A rodent strain inbred to over-express a particular gene may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which produces the number of organisms needed to satisfy statistical requirements.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. No. 4,736,866, U.S. Pat. No. 5,175,383 and U.S. Pat. No. 5,767,337.) In some cases, the introduced gene may be activated at a specific time in a specific tissue type during fetal development or postnatally. Expression of the transgene is monitored by analysis of phenotype, tissue-specific mRNA expression, and challenged with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene sequence which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Then transformed ES cells are selected under conditions, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev Biol 168:342–357; Wiles and Keller (1991) Development 111:259–267; and Klug et al. (1996) J Clin Invest 98:216–224). Recent developments demonstrate that ES cells derived from human blastocysts may also be manipulated in vitro to differentiate into eight separate cell lineages, including endoderm, mesoderm, and ectodermal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc Natl Acad Sci 95:11371–11376; Baudoin et al. (1998) Genes Dev 12:1202–1216; and Zhuang et al. (1998) Mol Cell Biol 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulatta*) and common marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolizers" and "poor metabolizers" of these agents.

In additional embodiments, the nucleic acid molecules which encode the mammalian protein may be used in any molecular biology techniques that have yet to be developed, provided the new techniques rely on properties of nucleic acid sequences that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the human meningioma cDNA library, MENTUNON3, is described.

I Representative cDNA sequence preparation

The normalized human meningioma cDNA library, MENTUNON3, was constructed from tissue obtained from a 35-year-old Caucasian female during a right suboccipital craniectomy. The frozen tissue was homogenized and lysed in guanidinium isothiocyanate solution using a POLYTRON homogenizer (Brinkmann Instruments, Westbury N.J.). The lysate was centrifuged over a 5.7 M CsCl cushion using an SW28 rotor in an L8-70M ultracentrifuge (Beckman Coulter, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNAse (Life Technologies) at 37° C. The RNA extraction and precipitation were repeated twice as before.

Messenger RNA (mRNA) was isolated using the OLIGOTEX kit (Qiagen, Valencia Calif.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were fractionated on a SEPHAROSE CL-4B column (APB), and those cDNAs exceeding 400 bp were ligated into the NotI and EcoRI sites of the pINCY plasmid (Incyte Genomics, Palo Alto Calif.). The plasmid was transformed into DH5α or ELECTROMAX DH10B competent cells (Life Technologies).

Plasmid DNA was released from the cells and purified using the REAL PREP 96 plasmid kit (Qiagen). The recommended protocol was employed except for the following changes: 1) the bacteria were cultured in 1 ml of sterile TERRIFIC BROTH (BD Biosciences, Sparks Md.) with carbenicillin at 25 mg/l and glycerol at 0.4%; 2) after inoculation, the cultures were incubated for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using either a MICROLAB 2200 system (Hamilton) or a HYDRA microdispenser (Robbins Scientific, Sunnyvale Calif.) in combination with DNA ENGINE thermal cyclers (MJ Research). The cDNAs were sequenced by the method of Sanger and Coulson (1975; J Mol Biol 94:441–448) using either an ABI PRISM 377 (Applied Biosystems) or MEGABACE 1000 sequencing system (APB). Most of the isolates were sequenced using standard ABI protocols and kits (Applied Biosystems) with solution volumes of 0.25×–1.0× concentrations. In the alternative, cDNAs were sequenced using solutions and dyes from APB.

II Identification, Extension, Assembly, and Analyses of the Sequences

Incyte clone 700137522 (SEQ ID NO:15) from the ZOOSEQ database (Incyte Genomics) of rat cDNA sequences, identified during analysis of differential expression of sequences in male reproductive tissues. Incyte clone 700137522 was used to identify first pass and extended cDNAs in the LIFESEQ database (Incyte Genomics), SEQ ID Nos:3–11, which were assembled using PHRAP (Green, University of Washington). The assembled sequence, SEQ ID NO:1 was translated using MACDNASIS PRO software (Hitachi Software Engineering) to show the coding region, SEQ ID NO:2. The nucleotide and amino acid sequences were queried against databases such as the GenBank databases, SwissProt, BLOCKS, PRINTS, Prosite, and PFAM using BLAST. Motif and HMM algorithms were used to perform functional analyses, and the antigenic index (Jameson-Wolf analysis) was determined using LASERGENE software (DNASTAR). Then, the clones and assembled sequence were compared using BLAST across all mammalian libraries to identify homologous nucleic acid sequences, SEQ ID NOs:12–16.

III Sequence Similarity

Sequence similarity was calculated as percent identity based on comparisons between at least two nucleic acid or amino acid sequences using the clustal method of the MEGALIGN program (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times one hundred. Gaps of very low or zero similarity between the two sequences are not included.

IV Northern Analysis

Northern analysis is a laboratory technique used to detect the presence of a transcript of a gene and involves the hybridization of a labeled probe to a membrane on which RNAs from a particular cell type or tissue have been bound.

Analogous computer techniques applying BLAST were used to search for identical or related molecules in GenBank or LIFESEQ databases (Incyte Genomics). Sequence-based analysis is much faster than membrane-based hybridization, and the sensitivity of the computer search can be modified to determine whether any particular match is categorized as exact or similar. The basis of the search is the product score which is defined as: (percent sequence identity×percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Nucleic Acid Sequences

The nucleic acid sequence of SEQ ID NO:1 was produced by assembly of first pass and extended clones. At least one of the Incyte cDNA clones was extended using oligonucleotide primers; one primer was synthesized to initiate 5' extension of the known fragment, and the other, to initiate 3' extension of the known fragment. The initial primers were designed using OLIGO 4.06 software (National Biosciences) to be about 22 to 30 nucleotides in length, to have a GC content of about 50%, and to anneal to the target sequence at temperatures of about 55° C. to about 68° C. Any fragment which would result in hairpin structures and primer-primer dimerizations was avoided. Selected human cDNA libraries were used to extend the sequence. If more than one extension is needed, additional or nested sets of primers are designed.

High fidelity amplification was obtained by performing PCR in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, parameters for the primer pair, T7 and SK+ (Stratagene), were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v); Molecular Probes) dissolved in 1×TE and 0.5 µl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (APB). For shotgun sequencing, the digested fragments were separated on about 0.6–0.8% agarose gels, fragments were excised as visualized under UV light, and agar removed/digested with AGARACE (Promega). Extended fragments were religated using T4 DNA ligase (New England Biolabs, Beverly Mass.) into pUC 18 vector (APB), treated with Pfu DNA polymerase (Stratagene) to fill-in restriction site overhangs, and transformed into competent E. coli cells. Transformed cells were selected on antibiotic-containing media, and individual colonies were picked and cultured overnight at 37° C. in 384-well plates in LB/2x carbenicillin liquid media.

The cells were lysed, and DNA was amplified using Taq DNA polymerase (APB) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (APB) or the ABI PRISM BIGDYE Terminator cycle sequencing ready reaction kit (Applied Biosystems).

In like manner, the nucleotide sequence of SEQ ID NO:1 is used to obtain regulatory sequences using the procedure above, oligonucleotides designed for outward extension, and a genomic DNA library.

VI Labeling of Probes and Hybridization Analyses

Substrate Preparation

Nucleic acid sequences are isolated from a biological source and applied to a substrate for standard nucleic acid hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20x saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 polymer (APB). Purified target nucleic acids are robotically arrayed onto a glass microscope slide (Corning Science Products, Corning N.Y.). The slide is previously coated with 0.05% aminopropyl silane (Sigma-Aldrich) and cured at 110° C. The arrayed glass slide (microarray) is exposed to UV irradiation in a STRATALINKER UV-crosslinker (Stratagene).

Probe Preparation cDNA probe sequences are made from mRNA templates. Five micrograms of mRNA is mixed with 1 µg random primer (Life Technologies), incubated at 70° C. for 10 minutes, and lyophilized. The lyophilized sample is resuspended in 50 µl of 1x first strand buffer (cDNA Synthesis systems; Life Technologies) containing a dNTP mix, [α-$^{32}$P] dCTP, dithiothreitol, and MMLV reverse transcriptase (Stratagene), and incubated at 42° C. for 1–2 hours. After incubation, the probe is diluted with 42 µl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 microcolumn (APB). Probes can be labeled with fluorescent markers, Cy3-dCTP or Cy5-dCTP (APB), in place of the radionuclide, [$^{32}$P]dCTP.

Hybridization

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probe sequences. After incubation at 65° C. for 48 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (APB), and the image is analyzed using IMAGEQUANT data analysis software (APB). To detect signals produced by a fluorescent probe hybridized on a microarray, the substrate is examined by confocal laser microscopy, and images are collected and analyzed using GEMTOOLS gene expression analysis software (Incyte Genomics).

VII Complementary Nucleic Acid Sequences

Sequences complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (PNAs). Oligonucleotides are designed using OLIGO 4.06 software (National Biosciences) and SEQ ID NO:1 or its fragments, SEQ ID NOs:3–11. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugiperda* (Sf9) insect cells with recombinant baculovirus, *Autographica californica* nuclear polyhedrosis virus. The polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (APB). Following purification, the GST moiety can be proteolytically cleaved from the mammalian protein at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (supra, unit 16). Purified mammalian protein obtained by these methods can be used directly in the following activity assay.

IX Functional Assays

Protein function is assessed by expressing the sequences encoding PTP at physiologically elevated levels in mammalian cell culture. The nucleic acid sequence is subcloned into PCMV SPORT vector (Life Technologies), which contains the strong cytomegalovirus promoter, and 5–10 µg of the vector is transformed into a endothelial or hematopoietic human cell line using transformation methods well known in the art. An additional 1–2 µg of a plasmid containing sequence encoding CD64-GFP (Clontech) is co-transformed to provide an fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells is separated using magnetic beads coated with either human IgG or antibody against CD64 (DYNAL, Lake Success N.Y.). mRNA is purified from the cells and analyzed by hybridization techniques.

X Production of PTP Specific Antibodies

PTP is purified using polyacrylamide gel electrophoresis and used to immunize rabbits. Antibodies are produced using protocols well known to those skilled in the art.

Alternatively, the amino acid sequence of PTP is analyzed using LASERGENE software (DNASTAR) to determine regions of high immunogenicity. An immunogenic epitope, usually found near the C-terminus or in a hydrophilic region is selected, synthesized, and used to raise antibodies by means known to those of skill in the art.

Typically, epitopes of about 15 residues in length are produced using an ABI 431A peptide synthesizer (Applied Biosystems) using Fmoc-chemistry and coupled to KLH (Sigma-Aldrich) by reaction with N-maleimidobenzoyl-N-hydroxysuccinimide ester to increase immunogenicity. Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radioiodinated goat anti-rabbit IgG. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbence of the protein. After coupling, the column is eluted using a buffer of pH 2–3 or a high concentration of urea or thiocyanate ion to disrupt antibody/protein binding, and the protein is collected.

XII Screening Molecules for Specific Binding with the Nucleic Acid Molecule or Protein The nucleic acid molecule, or fragments thereof, or the protein, or portions thereof, are labeled with $^{32}$P-dCTP, Cy3-dCTP, Cy5-dCTP (APB), or BIODIPY or FITC (Molecular Probes), respectively. Libraries of candidate molecules previously arranged on a substrate are incubated in the presence of labeled nucleic acid molecule or protein. After incubation under conditions for either a nucleic acid molecule or amino acid sequence, the substrate is washed, and any position on the substrate retaining label, which indicates specific binding or complex formation, is assayed, and the binding molecule is identified. Data obtained using different concentrations of the nucleic acid molecule or protein are used to calculate affinity between the labeled nucleic acid molecule or protein and the bound molecule.

XIII Demonstration of Protein Activity

PTP, or biologically active fragments thereof, are labeled with $^{125}$I Bolton-Hunter reagent (Bolton et al. (1973) Biochem J 133:529). Candidate molecules, including various PC molecular species, previously arrayed in the wells of a multi-well plate are incubated with the labeled PTP, washed, and any wells with labeled PTP complex are assayed. Data obtained using different concentrations of PTP are used to calculate values for the number, affinity, and association of PTP with the candidate molecules.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

---

SEQUENCE LISTING

```
<160> NUMBER OF SEQ ID NOS: 17

<210> SEQ ID NO 1
<211> LENGTH: 1865
<212> TYPE: DNA
<213> ORGANISM: Homo sapiens
<220> FEATURE:
<221> NAME/KEY: misc_feature
<223> OTHER INFORMATION: Incyte ID No: 1772859CB1

<400> SEQUENCE: 1
atcgttctgt ggtcctttct tttatgattc acaaggaatg accctcttca tcgcctctcc      60
taattcagtc ctcacaacag tccttttaca aatgggacaa caggttagag gaagtcaggc     120
agatttccag catcatagag agtaaaggac cagggaagga tcaggattca aggactgcac     180
ccaggctctg cttccagctt gctgtgtgac tttgggtaat tttgttccct tagggaactg     240
agctttctca tttgtaaatg caaacaggct gttgggagga tcaaatgaga tccagggtg      300 aaaacagctt agtttacttt caggaattta cccacgcggt atataaaggc aaaatattat     360
tatagtcagg tgattgtaga ttgaggaacc catttcctca tcctgcaaat tgcaaacctg     420
agggcccaaa gagggacagg ggcttgcccc aggtctcagc aggctgtgag caagagctaa     480
agcctaatcc tcctgccttt gggcctggag cccttccttg tacccaggg gtcagtgtct      540 ttgttggata caggcttaga ttgactgact gtaccctgag aacctagggg agtccctgtt     600
cccaattctt ctcctacccc caccttggcc tgatggagga agaccctgct gtgttgagat     660
gagcaccaga gccaagaagc tgaggaggat ctggagaatt ctggaggaag aggagagtgt     720
tgctggagct gtacagaccc tgcttctcag gtcccaggaa ggtggcgtca gcatctgcag     780
ccgcgtcgac gttgtcggag cctccgcgga ggacccagga gagccggact aggaccaggg     840
ccctgggcct ccccacactc cccatggaga agctggcggc ctctacagag ccccaagggc     900
```

```
ctcggccggt cctgggccgt gagagtgtcc aggtgcccga tgaccaagac tttcgcagct    960
tccggtcaga gtgtgaggct gaggtgggct ggaacctgac ctatagcagg gctggggtgt   1020
ctgtctgggt gcaggctgtg gagatggatc ggacgctgca caagatcaag tgccggatgg   1080
agtgctgtga tgtgccagcc gagacactct acgacgtcct acacgacatt gagtaccgca   1140
agaaatggga cagcaacgtc attgagactt ttgacatcgc ccgcttgaca gtcaacgctg   1200
acgtgggcta ttactcctgg aggtgtccca agcccctgaa gaaccgtgat gtcatcaccc   1260
tccgctcctg gctccccatg ggcgctgatt acatcattat gaactactca gtcaaacatc   1320
ccaaataccc acctcggaaa gacttggtcc gagctgtgtc catccagacg ggctacctca   1380
tccagagcac agggccaaag agctgcgtca tcacctacct ggcccaggtg gaccccaaag   1440
gctccttacc caagtgggtg gtgaataaat cttctcagtt cctggctccc aaggccatga   1500
agaagatgta caaggcgtgc ctcaagtacc ccgagtggaa acagaagcac ctgcctcact   1560
tcaagccgtg gctgcacccg gagcagagcc cgttgccgag cctggcgctg tcggagctgt   1620
cggtgcagca tgcggactca ctggagaaca tcgacgagag cgcggtggcc gagagcagag   1680
aggagcggat gggcggcgcg ggcggcgagg gcagcgacga cgacacctcg ctcacctgag   1740
cgccgcaccg cttcagggac ggagacagga ccgggcgagc cctggggcgg cggccgctcc   1800
tgcactttct cccctccccc acccggcacc tggtggcacc gggccaggcc caggcgggtg   1860
ctgca                                                               1865
```

<210> SEQ ID NO 2
<211> LENGTH: 291
<212> TYPE: PRT
<213> ORGANISM: Homo sapiens
<220> FEATURE:
<221> NAME/KEY: misc_feature
<223> OTHER INFORMATION: Incyte ID No: 1772859CD1

<400> SEQUENCE: 2

```
Met Glu Lys Leu Ala Ala Ser Thr Glu Pro Gln Gly Pro Arg Pro
  1               5                  10                  15

Val Leu Gly Arg Glu Ser Val Gln Val Pro Asp Asp Gln Asp Phe
                 20                  25                  30

Arg Ser Phe Arg Ser Glu Cys Glu Ala Glu Val Gly Trp Asn Leu
                 35                  40                  45

Thr Tyr Ser Arg Ala Gly Val Ser Val Trp Val Gln Ala Val Glu
                 50                  55                  60

Met Asp Arg Thr Leu His Lys Ile Lys Cys Arg Met Glu Cys Cys
                 65                  70                  75

Asp Val Pro Ala Glu Thr Leu Tyr Asp Val Leu His Asp Ile Glu
                 80                  85                  90

Tyr Arg Lys Lys Trp Asp Ser Asn Val Ile Glu Thr Phe Asp Ile
                 95                 100                 105

Ala Arg Leu Thr Val Asn Ala Asp Val Gly Tyr Tyr Ser Trp Arg
                110                 115                 120

Cys Pro Lys Pro Leu Lys Asn Arg Asp Val Ile Thr Leu Arg Ser
                125                 130                 135

Trp Leu Pro Met Gly Ala Asp Tyr Ile Ile Met Asn Tyr Ser Val
                140                 145                 150

Lys His Pro Lys Tyr Pro Pro Arg Lys Asp Leu Val Arg Ala Val
                155                 160                 165
```

```
Ser Ile Gln Thr Gly Tyr Leu Ile Gln Ser Thr Gly Pro Lys Ser
            170                 175                 180

Cys Val Ile Thr Tyr Leu Ala Gln Val Asp Pro Lys Gly Ser Leu
            185                 190                 195

Pro Lys Trp Val Val Asn Lys Ser Ser Gln Phe Leu Ala Pro Lys
            200                 205                 210

Ala Met Lys Lys Met Tyr Lys Ala Cys Leu Lys Tyr Pro Glu Trp
            215                 220                 225

Lys Gln Lys His Leu Pro His Phe Lys Pro Trp Leu His Pro Glu
            230                 235                 240

Gln Ser Pro Leu Pro Ser Leu Ala Leu Ser Glu Leu Ser Val Gln
            245                 250                 255

His Ala Asp Ser Leu Glu Asn Ile Asp Glu Ser Ala Val Ala Glu
            260                 265                 270

Ser Arg Glu Glu Arg Met Gly Gly Ala Gly Gly Glu Gly Ser Asp
            275                 280                 285

Asp Asp Thr Ser Leu Thr
            290
```

<210> SEQ ID NO 3
<211> LENGTH: 573
<212> TYPE: DNA
<213> ORGANISM: Homo sapiens
<220> FEATURE:
<221> NAME/KEY: misc_feature
<223> OTHER INFORMATION: Incyte ID No: 3591822F6

<400> SEQUENCE: 3

```
atcgttctgt ggtcctttct tttatgattc acaaggaatg accctcttca tcgcctctcc      60
taattcagtc ctcacaacag tccttttaca aatgggacaa caggttagag gaagtcaggc     120
agatttccag catcatagag agtaaaggac cagggaagga tcaggattca aggactgcac     180
ccaggctctg cttccagctt gctgtgtgac tttgggtaat tttgttccct tagggaactg     240
agctttctca tttgtaaatg caaacaggct gttgggagga tcaaatgaga tccaggggtg     300
aaaacagctt agtttacttt caggaattta cccacgcggt atataaaggc aaaatattat     360
tatagtcagg tgattgtaga ttgaggaacc catttcctca ttctgcaaat tgcaaacctg     420
agggcccaaa gagggacagg ggcttgcccc aggtctcagc aggctgtgag caagagctaa     480
agcctaatcc tcctgccttt gggcctggag cccttccttg taccccaggg gtcagtgtct     540
ttgttggata caggcttaga ttgactgact gta                                   573
```

<210> SEQ ID NO 4
<211> LENGTH: 516
<212> TYPE: DNA
<213> ORGANISM: Homo sapiens
<220> FEATURE:
<221> NAME/KEY: misc_feature
<223> OTHER INFORMATION: Incyte ID No: 745516R6
<221> NAME/KEY: unsure
<222> LOCATION: 46, 312, 351, 373, 453
<223> OTHER INFORMATION: a, t, c, g, or other

<400> SEQUENCE: 4

```
gcaggctgtg agcaagagct aaagcctaat cctcctgcct ttgggnctgg agccttcctt      60
gtaacccagc ggtcagtgtc tttgttggat acaggcttag attgactgac tgtaccctga     120
gaacctaggg gagtccctgt tcccaattct tctcctaccc ccaccttggc ctgatggagg     180
aagaccctgc tgtgttgaga tgagcaccag agccaagaag ctgaggagga tctggagaat     240
```

```
tctggaggaa gaggagagtg ttgctggagc tgtacagacc ctgcttctca ggtcccagga      300
aggtggcgtc anatctgcag ccgcgtcgac gttgtcggag cctccgcgga ngacccagg       360 agagccggac tangaccagg gccttgggct tcccaacttc ccatggagaa gctggcgggc      420
ttaagagccc aagggctcgc cgtctggcgt aanttcagtg ccatacaact tgagttcgta     480
attagtagtg tgactactta aggtggtttt tgtagc                                516

<210> SEQ ID NO 5
<211> LENGTH: 411
<212> TYPE: DNA
<213> ORGANISM: Homo sapiens
<220> FEATURE:
<221> NAME/KEY: misc_feature
<223> OTHER INFORMATION: Incyte ID No: 1807728F6
<221> NAME/KEY: unsure
<222> LOCATION: 63, 396, 406-408, 410
<223> OTHER INFORMATION: a, t, c, g, or other

<400> SEQUENCE: 5
ggcaccccgg ccccggcggg ccccggcgga cggcgggcaa aggtcccagg aaggtggcgt      60
canatctgca gccgcgtcga cgttgtcgga gcctccgcgg aggacccagg agagccggac      120
taggaccagg gccctgggcc tccccacact ccccatggaa aagctggcgg cctctacaga     180
gccccaaggg cctcggccgg tcctgggccg tgagagtgtc caggtgcccg atgaccaaga     240
ctttcgcagc ttccggtcag agtgtgaggc tgaggtgggc tggaacctga cctatagcag     300
ggctggggtg tctgtctggg tgcaggctgt ggagatggat cggacgctgc acaagatcaa     360
gtgccggatg gagtgctgtg atgtgccagc cgaganatct acgacnnncn a              411

<210> SEQ ID NO 6
<211> LENGTH: 248
<212> TYPE: DNA
<213> ORGANISM: Homo sapiens
<220> FEATURE:
<221> NAME/KEY: misc_feature
<223> OTHER INFORMATION: Incyte ID No: 1772859H1

<400> SEQUENCE: 6
gagtgtccag gtgcccgatg accaagactt tcgcagcttc cggtcagagt gtgaggctga     60
ggtgggctgg aacctgacct atagcagggc tggggtgtct gtctgggtgc aggctgtgga    120
gatggatcgg acgctgcaca agatcaagtg ccggatggag tgctgtgatg tgccagccga    180
gacactctac gacgtcctac acgacattga gtaccgcaag aaatgggaca gcaacgtcat     240
tgagactt                                                                248

<210> SEQ ID NO 7
<211> LENGTH: 277
<212> TYPE: DNA
<213> ORGANISM: Homo sapiens
<220> FEATURE:
<221> NAME/KEY: misc_feature
<223> OTHER INFORMATION: Incyte ID No: 1505466H1

<400> SEQUENCE: 7
agccgagaca ctctacgacg tcctacacga cattgagtac cgcaagaaat gggacagcaa    60
cgtcattgag acttttgaca tcgcccgctt gacagtcaac gctgacgtgg gctattactc   120
ctggaggtgt cccaagcccc tgaagaaccg tgatgtcatc accctccgct cctggctccc    180
catgggcgct gattacatca ttatgaacta ctcagtcaaa catcccaaat acccacctcg    240
```

```
gaaagattgg tccgagctgt gtccatccag acgggct                                   277
```

<210> SEQ ID NO 8
<211> LENGTH: 287
<212> TYPE: DNA
<213> ORGANISM: Homo sapiens
<220> FEATURE:
<221> NAME/KEY: misc_feature
<223> OTHER INFORMATION: Incyte ID No: 798614H1
<221> NAME/KEY: unsure
<222> LOCATION: 7, 28, 87, 97, 184, 198, 224, 277
<223> OTHER INFORMATION: a, t, c, g, or other

<400> SEQUENCE: 8

```
cgacgtncta cacgacattg agtaccgnaa gaaatgggac agcaacgtca ttgagactttt         60 tgacatcgac cgcttgacag tcaacgntga cgtgggntat tactcctgga ggtgtcccaa        120 gccccctgaag aaccgtgatg tcatcaacct tcggttctgg gttcccatgg gcgctgatta       180
catnattatg aactactnag tcaaacatcc caaataccca cctnggaaag acttggtccg        240
agctgtgtcc atccagacgg ggtacctgat tcagagnaca agggcca                      287
```

<210> SEQ ID NO 9
<211> LENGTH: 278
<212> TYPE: DNA
<213> ORGANISM: Homo sapiens
<220> FEATURE:
<221> NAME/KEY: misc_feature
<223> OTHER INFORMATION: Incyte ID No: 4114738H1
<221> NAME/KEY: unsure
<222> LOCATION: 46, 82-83, 201, 203, 222, 228
<223> OTHER INFORMATION: a, t, c, g, or other

<400> SEQUENCE: 9

```
ctcggaaaga cttggtccga gctgtgtcca tccagacggg ctaccncatc cagagcacag         60
ggcccaagag ctgcgtcatc annacctggc ccaggtggac cccaaaggct ccttacccaa        120
gtgggtggtg aataaatctt ctcagttcct ggctcccaag gccatgaaga agatgtacaa       180
ggcgtgcctc aagtaccccg ngnggaaaca gaagcacctg gnctcatnca agtgtggctg       240
cacccggagc agagcccgtt gccgagcctg gcgctgtc                                 278
```

<210> SEQ ID NO 10
<211> LENGTH: 278
<212> TYPE: DNA
<213> ORGANISM: Homo sapiens
<220> FEATURE:
<221> NAME/KEY: misc_feature
<223> OTHER INFORMATION: Incyte ID No: 1923871H1

<400> SEQUENCE: 10

```
caggcccaag agctgcgtca tcacctacct ggcccaggtg daccccaaag gctccttacc          60
caagtgggtg gtgaataaat cttctcagtt cctggctccc aaggccatga agaagatgta        120
caaggcgtgc ctcaagtacc ccgagtggaa acagaagcac ctgcctcact tcaagccgtg        180
gctgcacccg gagcagagcc cgttgccgag cctggcgctg tcggagctgt cggtgcagca        240
tgcggactca ctggagaaca tcgacgagag cgcggtgg                                 278
```

<210> SEQ ID NO 11
<211> LENGTH: 232
<212> TYPE: DNA
<213> ORGANISM: Homo sapiens
<220> FEATURE:
<221> NAME/KEY: misc_feature
<223> OTHER INFORMATION: Incyte ID No: 2013709H1

```
<221> NAME/KEY: unsure
<222> LOCATION: 61
<223> OTHER INFORMATION: a, t, c, g, or other

<400> SEQUENCE: 11
cggactcact ggagaacatc gacgagagcg cggtggccga gagcagagag gagcggatgg    60
ncggcgcggg cggcgagggc agcgacgacg acacctcgct cacctgagcg ccgcaccgct   120
tcagggacgg agacaggacc gggcgagccc tgggcggcg ccgctcctg cactttctcc    180 cctcccccac ccggcacctg gtggcacggg ccaggcccag gcgggtgctg ca           232

<210> SEQ ID NO 12
<211> LENGTH: 289
<212> TYPE: DNA
<213> ORGANISM: Rattus norvegicus
<220> FEATURE:
<221> NAME/KEY: misc_feature
<223> OTHER INFORMATION: Incyte ID No: 700488211H1
<221> NAME/KEY: unsure
<222> LOCATION: 37
<223> OTHER INFORMATION: a, t, c, g, or other

<400> SEQUENCE: 12
gacgccacct tcctgggacc tgtacgggct tcttgcnggg gcgggccggg gccggggtgc    60
gagctcttcc gccgcgccga cgttgtctga gcctccgcgg aggacccagg agagtcggac   120
taggaccagg gccccgggcc tccccacgct ctctatggaa aagccagctg cttcaacaga   180
accccaaggg cctcggcccg ctttgggccg tgaaagtgtc caggtgcccg atgaccagga   240
cttccgcagt tttcggtcag agtgtgaggc cgaggtggtg gaacctgac                289

<210> SEQ ID NO 13
<211> LENGTH: 279
<212> TYPE: DNA
<213> ORGANISM: Rattus norvegicus
<220> FEATURE:
<221> NAME/KEY: misc_feature
<223> OTHER INFORMATION: Incyte ID No: 700607704H1

<400> SEQUENCE: 13
aagtgtccag gtgcccgatg accaggactt ccgcagtttt cggtcagagt gtgaggccga    60
ggtgggctgg aacctgacct acagcaaggc cggtgtgtct gtgtgggtgc aggctgtgga   120
gatggatcga actctgcaca agatcaagtc aggatggaa tgctgtgacg taccagctga    180
gacgctctac gatgtcctgc acgacataga ataccgaaag aagtgggaca gtaatgtcat   240
cgagacattc gacatcgctc gactgactgt caacgctga                          279

<210> SEQ ID NO 14
<211> LENGTH: 272
<212> TYPE: DNA
<213> ORGANISM: Rattus norvegicus
<220> FEATURE:
<221> NAME/KEY: misc_feature
<223> OTHER INFORMATION: Incyte ID No: 701255162H1

<400> SEQUENCE: 14
cgacatcgct cgactgactg tcaacgctga cgtaggatat tactcctgga ggtgtcccaa    60 gccctgaag aaccgtgatg tcatcaccct ccgctcctgg ctccccatgg gcgctgatta   120
catcattatg aactactcag tgaaacaccc taaatacca cctcggaaag acttggtccg   180
agctgtgtcc atccagacgg gctacctcat ccagagcacg gggcccaaga gctgtgtcat   240
cacctacctg gcccaagtgg accccaaagg ct                                 272
```

<210> SEQ ID NO 15
<211> LENGTH: 239
<212> TYPE: DNA
<213> ORGANISM: Rattus norvegicus
<220> FEATURE:
<221> NAME/KEY: misc_feature
<223> OTHER INFORMATION: Incyte ID No: 700137522H1
<221> NAME/KEY: unsure
<222> LOCATION: 194
<223> OTHER INFORMATION: a, t, c, g, or other

<400> SEQUENCE: 15

```
tcctggcccc caaggccatg aagaagatgt acaaggcctg catcaagtac cctgagtgga      60
agcagaaaca ccagccacat ttcaagccat ggctgcaccc ggagcagagc ccgttaccca     120
gcctggcgct gtcagagctg tcggtgcaac acgcagactc actggagaac atcgacgaga     180
gcgccgtgac aganagccgg gaggagcggg cgggtggagc aggagagggc agcgatgac     239
```

<210> SEQ ID NO 16
<211> LENGTH: 270
<212> TYPE: DNA
<213> ORGANISM: Rattus norvegicus
<220> FEATURE:
<221> NAME/KEY: misc_feature
<223> OTHER INFORMATION: Incyte ID No: 701435117T1
<221> NAME/KEY: unsure
<222> LOCATION: 2, 5, 34, 52, 74, 83, 166, 216
<223> OTHER INFORMATION: a, t, c, g, or other

<400> SEQUENCE: 16

```
anctnagcag gagcccagtg cccccaaaag gcangtgggg gaaggagga antgcagaag       60 gctcagtgcc ccanggttcc acnccagtcc tgtcttggtc cttgaagaga ggcggttctc     120
aggtgagtga tgtgtcgtca tcgctgccct ctcctgctcc acccgnccgc tcctcccggc     180
tctctgtcac ggcgctctcg tcgatgttct ccagtnagtc tgcgtgttgc accgacagct     240
ctgacagcgc caggctgggt aacgggctct                                      270
```

<210> SEQ ID NO 17
<211> LENGTH: 174
<212> TYPE: PRT
<213> ORGANISM: Mus musculus
<220> FEATURE:
<221> NAME/KEY: misc_feature
<223> OTHER INFORMATION: Incyte ID No: g897786

<400> SEQUENCE: 17

```
Ile Tyr Arg Leu Leu Asp Gln Pro Ser Gly Leu Tyr Glu Tyr Lys
 1               5                  10                  15

Val Phe Gly Val Leu Glu Gly Cys Ser Pro Ala Leu Leu Ala Asp
                20                  25                  30

Val Tyr Met Asp Leu Asp Tyr Arg Lys Gln Trp Asp Gln Tyr Val
                35                  40                  45

Lys Glu Leu Tyr Glu Lys Glu Ser Asp Glu Gln Met Val Ala Tyr
                50                  55                  60

Trp Glu Val Lys Tyr Pro Phe Pro Leu Ser Asn Arg Asp Tyr Val
                65                  70                  75

Tyr Thr Arg Gln Arg Arg Asp Leu Asp Val Asp Arg Arg Lys Ile
                80                  85                  90

Tyr Val Val Leu Ala Gln Ser Ile Ser Ala Pro Gln Phe Pro Glu
                95                 100                 105
```

-continued

```
Lys Ser Gly Val Ile Arg Val Lys Gln Tyr Lys Gln Ser Leu Ala
            110                 115                 120

Ile Glu Ser Asp Gly Lys Lys Gly Ser Arg Val Phe Met Tyr Tyr
            125                 130                 135

Phe Asp Asn Pro Gly Gly Gln Ile Pro Ser Trp Leu Ile Asn Trp
            140                 145                 150

Ala Ala Lys Asn Gly Val Pro Asn Phe Leu Lys Asp Met Val Lys
            155                 160                 165

Ala Cys Gln Asn Tyr His Lys Lys Thr
            170
```

TABLE 1

| Nucleic Acid SEQ ID NO: | Incyte Clone Number | Nucleotide Length | Source | Library | Coverage | Percent Identity |
|---|---|---|---|---|---|---|
| 3 | 3591822F6 | 573 | Homo sapiens | 293TF5T01 | 1–573 | n/a |
| 4 | 745516R6 | 516 | Homo sapiens | BRAITUT01 | 459–981 | n/a |
| 5 | 1807728F6 | 411 | Homo sapiens | SINTNOT13 | 709–1122 | n/a |
| 6 | 1772859H1 | 248 | Homo sapiens | MENTUNON3 | 924–1171 | n/a |
| 7 | 1505466H1 | 277 | Homo sapiens | BRAITUT07 | 1097–1374 | n/a |
| 8 | 798614H1 | 287 | Homo sapiens | OVARNOT03 | 1112–1398 | n/a |
| 9 | 4114738H1 | 278 | Homo sapiens | UTRSTUT07 | 1333–1615 | n/a |
| 10 | 1923871H1 | 278 | Homo sapiens | BRSTTUT01 | 1393–1668 | n/a |
| 11 | 2013709H1 | 232 | Homo sapiens | TESTNOT03 | 1633–1865 | n/a |
| 12 | 700488211H1 | 289 | Rattus norvegicus | RATENOT01 | 710–1000 | 69.2 |
| 13 | 700607704H1 | 279 | Rattus norvegicus | RALINOH01 | 923–1201 | 87.4 |
| 14 | 701255162H1 | 272 | Rattus norvegicus | RALITXT03 | 1172–1443 | 95.2 |
| 15 | 700137522H1 | 239 | Rattus norvegicus | RALINOT01 | 1387–1669 | 84.9 |
| 16 | 701435117T1 | 270 | Rattus norvegicus | RALITXT06 | 1585–1859 | 67.8 |

What is claimed is:

1. An isolated and purified mammalian protein comprising the amino acid sequence of SEQ ID No: 2 with phospholipid transfer activity.

2. A composition comprising the protein of claim 1.

3. A method for using a protein to screen a plurality of molecules to identify a ligand which specifically binds the protein, the method comprising:
   a) combining the protein of claim 1 with the plurality of molecules under conditions to allow specific binding, and
   b) detecting specific binding, thereby identifying a ligand which specifically binds the protein.

4. The method of claim 3 wherein the plurality of molecules is selected from DNA molecules, RNA molecules, peptide nucleic acids, peptides, proteins, agonists, antagonists, antibodies, drug compound, inhibitors, mimetics, and pharmaceutical agents.

5. A method of using a protein to prepare a polyclonal antibody which specifically binds the protein, comprising:
   a) immunizing an animal with the protein of claim 1 under conditions to elicit an antibody response;
   b) isolating animal antibodies; and
   c) screening the isolated antibodies with the protein thereby identifying a polyclonal antibody specifically binds the protein.

6. A method of using a protein to make a monoclonal antibody which specifically binds the protein comprising:
   a) immunizing an animal with the protein of claim 1 under conditions to elicit an antibody response;
   b) isolating antibody-producing cells from the animal;
   c) fusing the antibody-producing cells with immortalized cells in culture to form monoclonal antibody-producing hybridoma cells;
   d) culturing the hybridoma cells; and
   e) isolating from the culture monoclonal antibodies which specifically bind the protein.

7. A method of using a protein to purify a pharmaceutical agent which specifically binds the protein, the method comprising:
   a) providing a sample,
   b) combining the protein of claim 2 with the sample under conditions to allow specific binding,
   c) recovering the bound protein, and
   d) separating the bound protein, thereby obtaining purified pharmaceutical agent.

* * * * *